United States Patent [19]

Merat et al.

[11] Patent Number: 5,126,136

[45] Date of Patent: Jun. 30, 1992

[54] SKIN PROTECTION LOTION

[76] Inventors: Pierre H. Merat, P.O. Box 4710, San Luis Obispo, Calif. 93401-4710; Ralph Akyuz, 1805 W. 208 St. #201, Torrance, Calif. 90501

[21] Appl. No.: 701,196

[22] Filed: May 16, 1991

Related U.S. Application Data

[63] Continuation-in-part of Ser. No. 459,748, Aug. 5, 1988, abandoned.

[51] Int. Cl.⁵ .................................................. A61K 7/40
[52] U.S. Cl. .................................... 424/401; 424/47; 514/873; 514/938; 252/356; 252/357
[58] Field of Search ............................. 424/47, 63, 70; 252/356, 357, 351; 514/828, 848, 938, 873

[56] References Cited

U.S. PATENT DOCUMENTS

| | | | |
|---|---|---|---|
| 4,305,936 | 12/1981 | Klein | 514/179 |
| 4,389,418 | 6/1983 | Burton | 514/770 |
| 4,507,279 | 3/1985 | Okuyama et al. | 424/63 |
| 4,548,810 | 10/1985 | Zafchak | 424/70 |
| 4,761,276 | 8/1988 | Murray et al. | 424/59 |

Primary Examiner—Thurman K. Page
Assistant Examiner—Amy Hulina
Attorney, Agent, or Firm—Albert O. Cota

[57] ABSTRACT

A skin protection lotion consisting of a water phase mixture and an oil phase mixture. The two mixtures are mixed together to form a lotion concentrate. The lotion concentrate may be aerosolized in a can that then dispenses a mousse. Either the lotion or the mousse may be applied to an area of skin, such as the hands, to form a thin protective coating that protects the skin from a wide range of hazardous fluids.

6 Claims, No Drawings

SKIN PROTECTION LOTION

CROSS-REFERENCE TO RELATED APPLICATION

This application is a continuation-in-part of application Ser. No. 07/459,748 filed Aug. 5, 1988 now abandoned.

TECHNICAL FIELD

The invention pertains to chemical protection means for human skin and more particularly to a lotion or mousse for protecting human skin, such as hands and the like, from injury or stain due to acids or corrosive substances and to a method of formulating and applying same.

BACKGROUND ART

In many household chores and industrial activities, it is necessary for people to expose their skin, and especially their hands, to hostile environments wherein the skin or hands may become soiled, stained or injured by reason of chemical reactions or the like. For many years, people have searched for methods or means to protect exposed skin, especially hands, from such unpleasant or dangerous conditions. Rubber or plastic gloves have been proposed to overcome such hazards. However, many gloves are bulky and clumsy and interfere significantly with the wearer's sense of touch. Various lotions or hand creams have been proposed heretofore. However, these have usually been designed for highly specific protection and have failed to provide broad protection, as may be needed where the identity of the hostile substance is unknown. In other words, none of the prior art protective lotions etc. have provided protection for a broad range of potential hazards.

In contrast, the instant invention proposes a lotion or mousse containing a protective wax and suitable wetting and emulsifying agents, together with a moisture barrier agent and suitable antiseptics, astringents, anti-bacterial agents and emollients to form a thin protective coating over the treated area which will provide protection against a wide range of hostile or hazardous substances.

A search of the prior art did not disclose any patents that read directly on the claims of the instant invention however, the following U.S. patents were considered related:

| U.S. PAT. NO. | INVENTOR | ISSUED |
| --- | --- | --- |
| 2,310,889 | Becker | 9 February 1943 |
| 4,255,500 | Gould | 10 March 1981 |
| 4,305,936 | Klein | 15 December 1981 |
| 4,389,418 | Burton | 21 June 1981 |
| 4,463,156 | McGary et al | 31 July 1984 |
| 4,507,279 | Okuyama et al | 26 March 1985 |
| 4,548,810 | Zofchak | 22 October 1985 |

Each of the above patents discloses a formulation for a protective lotion or cream which is directed at providing protection against a specific type of hazard. However, none of the references suggests a product which provides protection against a wide range of hostile or hazardous substances.

DISCLOSURE OF THE INVENTION

The instant invention discloses a lotion or mousse that is formulated with a protective wax, an emollient and emulsifying agents, together with a moisture barrier agent and suitable antiseptics, astringents and anti-bacterial agents. The lotion or mousse when applied to the skin, will form a thin protective coating over the treated area which provides protection against a wide range of hostile or hazardous substances. The wetting and emulsifying agents serve to distribute the lotion over the treated area in a thin layer which prevents undesirable substances from penetrating through the layer to reach the protected area underneath. The moisture barrier agent also serves to prevent many undesirable substances from reaching the protected area, while the antiseptics, astringents and anti-bacterial agents serve to counteract or attack many undesirable substances. Thus, the inventive skin protection lotion serves to provide protection against a wide range of hostile or hazardous substances without requiring that the user be aware of the specific substances encountered.

Accordingly, it is an object of the instant invention to provide improved chemical protection means for human skin, hands and the like that uses sodium stearate as a water proofing and barrier compound.

Another object of the instant invention is to provide chemical protection for human skin, hands and the like against a wide range of hostile or hazardous substances.

An additional object of the instant invention is to provide a preparation for human skin, hands and the like, in the nature of a cream or mousse which can be spread on an area to be protected to provide protection against a wide range of hostile or hazardous substances.

A specific object of the instant invention is to provide a lotion or mousse containing a wax and suitable wetting and emulsifying agents, together with a moisture barrier agent and suitable antiseptics, astringents, anti-bacterial agents and emollients to form a thin protective coating over the treated area which will provide protection against a wide range of hostile or hazardous substances.

These and other objects and features of the instant invention will be apparent from the following detailed description.

BEST MODE FOR CARRYING OUT THE INVENTION

The best mode for carrying out the invention is presented in terms of a protective lotion that is prepared by mixing a water phase consisting 1.5–2.0% Sodium Stearate and 1.0–4.0% Stearoxytrimethylsilane as water proofing and barrier compounds; 3.0–4.0% Stearic acid as a primary emulsifier; 1.0–1.5% Triethanolamine as a secondary emulsifier; about 0.35% of a preservative and between 88.0–94.0% deionized water.

The above preservative may be comprised of a combination of Methylparaben and Propylparaben. Additionally to the lotion may be added:

4.0–6.0% Dimethylsiloxane as an emollient, 1.0–4.0% Dimethiconol Poly[oxy(dimethylsilylene)], α-hydro-ω-hydroxy as a film former and water proofing compound, 1.0–7.0% Polydimethylcyclosiloxane as a spreading agent; and 1.0–3.0% Amodimethicone Amino-polysiloxanes emulsion as a non-slip binder.

The above elements are mixed and heated to 75°–80° C. for approximately 15 minutes to form an emulsion. The emulsion is then allowed to cool to 40° C. after which, if desired, a suitable fragrance may be added and the emulsion packaged for distribution and sale. For this purpose, approximately 85% of the emulsion may be mixed with approximately 15% alcohol (SDA-40) to form a lotion concentrate or, if desired, approximately 88% of the lotion concentrate may be aerosolized in a can with approximately 12% of a propellant, such as an Isobutane/Propane mixture, to form a mousse.

In use, an approximately one inch sphere of the lotion or mousse is applied to the skin area to be protected and is rubbed about the area to assure that the area to be protected is thoroughly covered. When this is accomplished, the wetting agent and the emulsifiers serve to distribute the lotion or mousse over the protected area, in a thin layer, which precludes hostile or hazardous substances from reaching the protected skin.

Virtually all hostile and hazardous materials are precluded, by this thin layer, from reaching the protected area of skin. In fact, on numerous occasions, the applicant has applied the lotion to his hands and has demonstrated its effectiveness by pouring a non-concentrated sulfuric acid and various caustic substances directly over their hands without any harmful results. Furthermore, it has been found that the lotion concentrate of the instant invention continues to provide such protection for up to 4 to 5 hours and will last through several normal washings without loss of protection. Obviously, care must be taken to assure that the skin area to be protected is thoroughly covered with the lotion concentrate. Moreover, it will be apparent that repeated applications of the lotion concentrate will provide greater surety of protection.

If desired, additional protective materials may be added to the basic lotion concentrate described above. Thus, for example, 0.1-0.2% Aluminum Acetate may be added during preparation of the water phase as an antiseptic and astringent. Similarly, if desired, a suitable moisture barrier, such as a polymer of Hexadecene and Vinylpyrrolidone monomers, available from GAF Industries under the trademark "Ganex V-216" may be added to the oil phase to provide additional protection. Also, if desired, an anti-bacterial agent, such as Benzalkonium Chloride, may be added to the lotion concentrate for yet further protection. Again, if desired, suitable emollients, such as Isostearyl Neopentanoate, or other skin softening or smoothing agents may be added.

EXAMPLE 1

In one formulation of the lotion concentrate of the instant invention, a water phase comprising 1.5% Triethanolamine, 1.5% Sodium Stearate, and 0.2% Methylparaben were mixed with sufficient deionized water to form a mixture which was then heated to 75°-80° C. Meanwhile, an oil phase comprising 3.0% Stearic Acid, 1.5% Stearoxytrimethylsilane, and 0.15% Propylparaben were mixed together and heated to 75°-80° C. The water and oil phase mixtures were then mixed for 15 minutes and allowed to cool to 40° C., after which 0.4% of a suitable fragrance was added to complete the formulation.

EXAMPLE 2

In a second formulation of the lotion concentrate of the instant invention, a water phase was formed by mixing 1.5% Triethanolamine, 1.5% Sodium Stearate, and 0.2% Methylparaben with sufficient deionized water to form a mixture which was then heated to 75°-80° C. Meanwhile, an oil phase comprising 3.0% Stearic Acid, 1.5% Stearoxytrimethylsilane, 0.15% Propylparaben, and 4.5% Dimethylsiloxane as an emollient were mixed together and heated to 75°-80° C. The water and oil phase mixtures were then mixed for 15 minutes and allowed to cool to 40° C., after which 0.4% of a suitable fragrance was added to complete the formulation.

EXAMPLE 3

In a third formulation of the lotion concentrate of the instant invention, a water phase was formed by mixing 1.5% Triethanolamine, 1.5% Sodium Stearate, and 0.2% Methylparaben were mixed with sufficient deionized water to form a mixture which was then heated to 75°-80° C. Meanwhile, an oil phase comprising 3.0% Stearic Acid, 2.5% Dimethiconol Poly[oxy(dimethylsilylene)], α-hydro-ω-hydroxy as a film former and water proofing compound. 0.15% Propylparaben, and 4.5% Dimethylsiloxane as an emollient were mixed together and heated to 75°-80° C. The water and oil phase mixtures were then mixed for 15 minutes and allowed to cool to 40° C., after which 0.4% of a suitable fragrance was added to complete the formulation.

EXAMPLE 4

In a fourth formulation of the lotion concentrate of the instant invention, a water phase comprising 1.5% Triethanolamine, 1.5% Sodium Stearate, and 0.2% Methylparaben were mixed with sufficient deionized water to form a mixture which was then heated to 75°-80° C. Meanwhile, an oil phase comprising 3.0% Stearic Acid, 1.5% Stearoxytrimethylsilane, 0.15% Propylparaben, 2.5% Polydimethylcyclosiloxane as a spreading agent and 1.0% Amodimethicone as a non-slip binder were mixed together and heated to 75°-80° C. The water and oil phase mixtures were then mixed for 15 minutes and allowed to cool to 40° C., after which 0.4% of a suitable fragrance was added to complete the formulation.

EXAMPLE 5

In a fifth formulation of the lotion concentrate of the instant invention, a water phase comprising 1.5% Triethanolamine, 1.5% Sodium Stearate, and 0.2% Methylparaben were mixed with sufficient deionized water to form a mixture which was then heated to 75°-80° C. Meanwhile, an oil phase comprising 3.0% Stearic Acid, 1.5% Stearoxytrimethysilane, 0.15% Propylparaben, 2.0% Dimethylsiloxane as an emollient, 1.0% Dimethiconol Poly[oxy(dimethylsilylene)], α-hydro-ω-hydroxy as a film former and water proofing compound, 2.8% Polydimethylcyclosiloxane as a spreading agent and 4.0% Amodimethicone Amino-polysiloxanes emulsion as a non-slip binder were mixed together and heated to 75°-80° C. The water and oil phase mixtures were then mixed for 15 minutes and allowed to cool to 40° C., after which 0.4% of a suitable fragrance was added to complete the formulation.

EXAMPLE 6

In a sixth formulation of the lotion concentrate of the instant invention, a water phase comprising 1.0% Triethanolamine, 2.0% Sodium Stearate, 3.0% Stearic Acid, 0.20% Benzyl dimethyl stearyl ammonium chloride, 1.0% Benzalkonium chloride, 0.5% Nonoxynol-12, 1.0% Aluminum acetate, 0.2% Methylparaben, and 0.15% Propylparaben were mixed with sufficient deionized water to form a mixture which was then heated to 75°-80° C. Meanwhile, an oil phase comprising 3.0%

Stearoxytrimethylsilane, 4.0% Dimethylsiloxane, 2.0% Dimethiconol Poly[oxy(dimethylsilylene)], α-hydro-ω-hydroxy, 1.0% Cyclic dimethyl polysiloxane, 4.0% Polydimethylcyclosiloxane, and 1.0% Amodimethicone Amino-polysiloxanes emulsion were mixed together and heated to 75°-80° C. The water and oil phase mixtures were then mixed for 15 minutes and allowed to cool to 40° C., after which 0.4% of a suitable fragrance was added to complete the formulation.

EXAMPLE 7

In a seventh formulation of the lotion concentrate of the instant invention, a water phase comprising 1.5% Triethanolamine, 4.0% Stearic Acid, 0.1% Benzalkonium chloride, 0.2% Nonoxynol-12, 1.0% Aluminum Acetate, and 0.25% Methylparaben were mixed with sufficient deionized water to form a mixture which was then heated to 75°-80° C. Meanwhile, an oil phase comprising 4.0% Stearoxytrimethylsilane, 6.0% Dimethylsiloxane, 2.0% Dimethiconol, Poly[oxy(dimethylsilylene)], α-hydro-ω-hydroxy 5.0% Polydimethylcyclosiloxane, 0.2% Benzyl dimethyl stearyl ammonium chloride, 1.0% Amodimethicone, Amino-polysiloxanes emulsion and 0.15% Propylparaben were mixed together and heated to 75°-80° C. The water and oil phase mixtures were then mixed for 15 minutes and allowed to cool to 40° C., after which 0.4% of a suitable fragrance and 15.0 Ethanol as a solvent were added to complete the formulation. To convert to an aerosolized form, the finished formulation is then filled into the aluminum can and sealed by an appropriate valve. 2.0% Isobutane, 10.0% Butane, and 3.0% Propane, all as propellants, were introduced into the can by means of a pressurized system. This procedure develops into a finished product which dispenses as a thick, creamy lather.

Obviously, numerous other variation and modifications can be made without departing from the spirit of the instant invention. Therefore, it should be clearly understood that the forms of the instant invention described above are illustrative only and are not intended to limit its scope.

We claim:

1. A skin protection lotion that functions as a water proofing and barrier compound to prevent hostile and hazardous materials from affecting the skin, said lotion comprising:
   a) 88.0–94.0% deionized water,
   b) 3.0–4.0% stearic acid as a primary emulsifier,
   c) 1.5–2.0% sodium stearate as a water proofing and barrier compound,
   d) 1.0–1.5% triethanolamine as a secondary emulsifier,
   e) about 0.35% of a preservative, and
   f) 1.0–4.0% stearoxytrimethylsilane as a water proofing and barrier compound,
   g) 2.0–7.0% dimethylsiloxane as an emollient,
   h) 1.0–4.0% poly[oxy(dimethylsilylene)], -hydro -hydroxy as a film former and waterproofing compound
   i) 1.5–6.0% polydimethylcyclosiloxane as a spreading agent, and,
   j) 2.0–5.0% amino-polysiloxanes emulsion as a non-slip binder.

2. The lotion as specified in claim 1 wherein said preservative comprises a combination of methylparaben and propylparaben.

3. The lotion as specified in claim 1 further comprising:
   a) 0.10–0.50% benzyl dimethyl stearyl ammonium chloride as a compound for skin conditioning,
   b) 1.0–5.0% benzalkonium chloride as an anti-bacterial agent and,
   c) 0.01–0.20% nonoxynol-12, as a foaming agent.

4. A skin protection lotion that functions as a water proofing and barrier compound to prevent hostile and hazardous materials from affecting the skin, said lotion comprising:
   a) 64.0–85.0% deionized water,
   b) 3.0–4.0% stearic acid as a primary emulsifier,
   c) 1.5–2.0% sodium stearate as a water proofing and barrier compound,
   d) 1.0–1.5% triethanolamine as a secondary emulsifier,
   e) about 0.35% of a compound consisting of methylparaben and propylparaben as a preservative,
   f) 1.0–4.0% stearoxytrimethylsilane as a water proofing and barrier compound,
   g) 4.0–6.0% dimethylsiloxane as an emollient,
   h) 1.0–4.0% poly[oxy(dimethylsilylene)], α-hydro-ω-hydroxy and 1.0–3.0% cyclic dimethyl polysiloxane as film former and water proofing compounds,
   i) 2.0–8.0% polydimethylcyclosiloxane as a spreading agent,
   j) 1.0–4.0% amino-polysiloxanes emulsion as a non-slip binder,
   k) 0.01–0.20% benzyl dimethyl stearyl ammonium chloride as a compound for skin conditioning,
   l) 1.0–5.0% benzalkonium chloride as an anti-bacterial agent,
   m) 0.01–0.50% nonoxynol-12 as a foaming agent, and
   n) 0.001–1.0% aluminum acetate as a water proofing agent.

5. A skin protection lotion that functions as a water proofing and barrier compound to prevent hostile and hazardous materials from affecting the skin, said lotion comprising:
   a) 32.0–80.0% deionized water,
   b) 3.0–4.0% stearic acid as a primary emulsifier,
   c) 1.5–2.0% sodium stearate as a water proofing and barrier compound,
   d) 1.0–1.5% triethanolamine as a secondary emulsifier,
   e) about 0.35% of a preservative,
   f) 1.0–4.0% stearoxytrimethylsilane as a water proofing and barrier compound,
   g) 1.0–3.0% amino-polysiloxanes emulsion as a non-slip binder,
   h) 0.10–0.50% benzalkonium chloride as an anti-bacterial agent,
   i) 0.01–0.20% nonoxynol-12 as a foaming agent,
   j) 0.001–1.00% aluminum acetate as a water proofing agent,
   k) 9.0–15.0% ethanol as a solvent or carrier,
   l) 1.0–12.0% butane,
   m) 2.0–12.0% isobutane, and
   n) 1.0–12.0% propane as propellants.

6. A skin protection lotion that functions as a water proofing and barrier compound to prevent hostile and hazardous materials from affecting the skin, said lotion comprising:
   a) 15.0–72.0% deionized water,
   b) 3.0–4.0% stearic acid as a primary emulsifier,
   c) 1.0–1.5% triethanolamine as a secondary emulsifier,
   d) about 0.35% of a compound consisting of methylparaben and propylparaben as a preservative, e) 1.0–4.0% stearoxytrimethylsilane as a water proofing and barrier compound,
f) 4.0–6.0% dimethylsiloxane as an emollient,
g) 2.0–5.0% poly[oxy(dimethylsilylene)]α-hydro-ω-hydroxy as a film former and water proofing agent,
h) 3.0–8.0% polydimethylcyclosiloxane as a spreading agent,
i) 0.10–0.50% benzyl dimethyl stearyl ammonium chloride as a skin conditioning agent,
j) 9.0–15.0% ethanol as a solvent,
k) 1.0–12.0% butane, 1.0–12.0% isobutane and 1.0–12.0% propane as propellants,
l) 1.0–3.0% amino-polysiloxanes emulsion as a non-slip binder,
m) 0.10–0.50% benzalkonium chloride as a anti-bacterial agent,
n) 0.01–0.20% nonoxynol-12 as a foaming agent, and
o) 0.001–1.00% aluminum acetate as a water proofing agent.

* * * * *